(12) United States Patent
Rogasch et al.

(10) Patent No.: US 7,541,047 B2
(45) Date of Patent: Jun. 2, 2009

(54) METHOD FOR PRODUCTION OF SHAPED BODY FOR TREATING WOUNDS IN MILK PRODUCING ANIMALS

(76) Inventors: Rainer Rogasch, Wildunger Strasse 9, 34513 Waldeck (DE); Friedrich Fisseler, Schöne Aussicht 4a, 34516 Vöhl (DE); Marc Schmieding, Moersstrasse 2, 34497 Korbach (DE)

( * ) Notice: Subject to any disclaimer, the term of this patent is extended or adjusted under 35 U.S.C. 154(b) by 649 days.

(21) Appl. No.: 11/143,609

(22) Filed: Jun. 3, 2005

(65) Prior Publication Data

US 2005/0226903 A1 Oct. 13, 2005

Related U.S. Application Data

(63) Continuation of application No. 10/110,431, filed on Aug. 26, 2002, now abandoned.

(51) Int. Cl.
*A61F 2/00* (2006.01)
*A61K 9/14* (2006.01)

(52) U.S. Cl. ...................... 424/423; 424/486
(58) Field of Classification Search ................ 119/852
See application file for complete search history.

(56) References Cited

U.S. PATENT DOCUMENTS

| 4,344,968 A | 8/1982 | Aoda et al. |
| 4,347,237 A | 8/1982 | Evenstad et al. |
| 4,698,359 A | 10/1987 | Niederer et al. |
| 4,874,774 A | 10/1989 | Ushimaru et al. |
| 4,935,248 A * | 6/1990 | Witkin ....................... 424/616 |
| 5,248,700 A | 9/1993 | Lance |
| 5,393,738 A | 2/1995 | Vonderscher et al. |
| 5,700,486 A | 12/1997 | Canal et al. |
| 5,783,555 A | 7/1998 | Suzuki et al. |
| 5,874,479 A | 2/1999 | Martin |
| 6,068,855 A | 5/2000 | Leslie et al. |
| 6,117,455 A | 9/2000 | Takada et al. |

FOREIGN PATENT DOCUMENTS

| DE | 3230602 | | 2/1984 |
| GB | 887872 | * | 1/1962 |
| WO | 00/03660 | | 1/2000 |

OTHER PUBLICATIONS

G. Regdon, Jr., et al., "Formulation and in vitro study of theophylline containing suppositories", XP 000582508, 996 Die Pharmazi, 51 (1996) May, No. 5 Eschborn, DE, pp. 347-352.

* cited by examiner

*Primary Examiner*—Johann R Richter
*Assistant Examiner*—Christopher R Lea
(74) *Attorney, Agent, or Firm*—Clark & Brody

(57) ABSTRACT

Water-dispersible or water-soluble polymers, particularly those of the family of compounds comprising the poloxamers or the polyesters or amphiphilic agents (emulsifiers), and also lipophilic materials are dispersed by melting the components at suitable temperatures with admixture of pharmaceutically active substances by mechanical precedures, i.e. a lipophilic dispers phase is distributed in a hydrophilic continuous polymer phase to form a stable dispersion. By controlled cooling, curing, and storage followed by high-pressure molding at defined temperatures and operating pressures there are produced, in addition to other types of shaped bodies, dispersed polymeric fatty sticks distinguished by particularly good fracture strength, flexibility, and variable time-specific dimensional stability.

1 Claim, No Drawings

METHOD FOR PRODUCTION OF SHAPED BODY FOR TREATING WOUNDS IN MILK PRODUCING ANIMALS

This application is a continuation of U.S. patent application Ser. No. 10/110,431 which was filed Aug. 26, 2002 now abandoned.

FIELD OF THE INVENTION

The invention relates to a shaped body for medicinal use in body cavities and/or wound cavities in humans or animals, to a method of producing said shaped bodies, and to a method of using the same.

Pharmaceutical or medical sticks (shaped bodies) are an old pharmaceutical dosage form, usually obtained by casting and curing suitable pharmaceutical auxiliary materials in appropriate casting molds. A frequently used special form of medical sticks comprises suppositories for anal or rectal administration, these usually being produced on the basis of triglycerides. Since triglycerides (fats) tend to become brittle, it is hardly possible to use these materials for making sticks of lasting non-breakability having a diameter of less than 4 mm and lengths of more than 20 mm.

In order to counteract this, it might be possibly to use pure blends of plastics material and active agent and to extrude them to produce sticks of any diameter. Such sticks would indeed have adequate fracture strength and high elasticity and would thus have the desired material characteristics, but they would suffer from serious drawbacks with regard to their compatibility in physiological compartments, since plastics materials are degradable only to a small extent or not at all. If on the other hand the carrier degrades too quickly, the desired compartment will not, in most cases, be supplied with the necessary medicinal substance to an adequate extent, which may spoil the wound healing effect.

These handicaps are counteracted in Patent Application EP-A 1,064,514 by adding polyethylene glycols acting as amphiphilic agents. Despite the resulting increased elasticity of the shaped body formed, it is not possible to dispersely stabilize large concentrations, by weight, of lipids or fatty acids in the shaped body and thus to vary the release rate of various polar pharmaceutically active substances over a wide range.

It is an object of the present invention to avoid these and other prior art drawbacks and to provide shaped bodies for medical administration in body cavities and/or wound cavities in humans or animals, which shaped bodies show high elasticity and a high fracture strength and release the active substances or combinations of active substances present therein at a constant rate over a quite long period of time.

A shaped body for medical administration in body cavities and/or wound cavities in humans or animals, comprising at least one amphiphilic continuous phase, for example, a water-dispersible polymer, and at least one lipophilic component as disperse phase and also comprising at least one pharmaceutically effective water-soluble or fat-soluble material, is characterized, according to the present invention, in that the continuous phase is a biologically neutral oligomer, for example, a copolymer, of a polyether. By this means the shaped body is imparted with exceptionally high elasticity and fracture strength, which is particularly important for its introduction into a body cavity or wound cavity. This also ensures stabilization of relatively high concentrations, by weight, of the lipophilic dispers phase. The shaped body is capable of residing in the desired compartment for many hours and of releasing its content of (pharmaceutically) active substances (in retarded manner) to the environment over a long period of time. The curative action is exceptional good. The use of a biologically neutral oligopolyether ensures that no undesirable reciprocal effects occur with the environment.

The continuous phase is an ether-like block oligopolymer having at least two consecutively linked sets of blocks of various alkoxyl groups, for example, a block copolymer. This class of substances having the general empirical formula

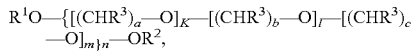

in which k, m≧50 and L≧20 and also a, b, and c=1 to 6, where a, c≠b and in which $R^1$, $R^2$=H, alkyl, aryl and $R^3$=H, methyl, and having the polaxamer-typical formula

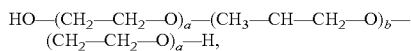

in which a=2 to 130 and b=15 to 67, is distinguished by the fact that lipophilic contents such as beeswax or triglycerides can be mixed therewith in high concentrations of up to 52 wt % to give homogeneous dispersions without the shaped body losing the elasticity or fracture strength necessary for its introduction into the cavity, which is of particular significance for the present invention. The block copolymer can be a poloxamer, for example, poloxamer 124, poloxamer 188, poloxamer 237, poloxamer 338, or poloxamer 407.

In the embodiment for which independent protection is claimed, the invention provides that the continuous phase is a biologically neutral polyester. The latter, depending on its structure, is more or less readily hydrolytically cleavable, which also applies to polyanhydrides and polyamide ester to various extents. It is preferred to use biodegradable copolymeric or oligopolymeric structures, and use may also be made of block copolymers and block oligopolymeric forms. These molecules are on account of their heterogeneous periodic structure particularly suitable for the production of shaped bodies containing active substance, since specific selection of these polymers can precisely adjust the rate of degradation thereof and thus that of the shaped body in the tissue compartment. In this way it is easy to achieve uniform release of active substance into the organism over a specific period of time. Another advantage consists in that the monomers forming in the tissue compartment as a result of degradation can be metabolized by the body.

The continuous phase is a thermoplastic polyester, for example, a polyortho ester, a polylactic acid in the D, L or D/L form, a polyglycolide, a poly(ε-caprolactone), a polydioxanone, a polytrimethylene carbonate, a polyhydroxybutyrate, or a polyhydroxyvalerate. The polyester can be an oligopolymer or a block oligopolymer composed of at least two different monomers, for example, a copolymer or a block copolymer.

In another independent embodiment of the invention the continuous phase comprises at least one biologically neutral, non-ionic or neutrally charged emulsifier. Here again, there are obtained shaped bodies which despite large lipophilic contents have a high degree of elasticity and fracture strength. Biologically acceptable, neutrally charged or non-ionic emulsifiers, i.e. detergents, such as CHAPS, Tween®, or Span® can be used in the continuous phase as amphiphilic components, which is particularly advantageous when the shaped body is not an oral administration form. They form association colloids in which otherwise very difficultly stabilizable pharmaceutically active species can be very easily introduced.

It is expedient to use emulsifiers having a high CMC, e.g., octyl glucoside or dodecyl maltoside, since such surfactants avoid excessive foam formation and, in particular, avoid cell lysis at the site of action. The CMC should be, say, greater than 6.

If very long residence times of the shaped body in the desired compartment are required or if the pharmaceutically active substance is required to be released extremely slowly from the shaped body, the continuous phase comprises a biologically neutral polyanhydride, polyester amide, or polyamide or comprises an oligopolymer or copolymer containing oligomeric or polymeric D-amino acid regions. The decisive factor here is the use of chemically and mechanically more stable amphiphilic polymers in the formulation. Particularly suitable are polyamides or polypeptides and polyester amides comprising D-amino acids. Oligopolymeric or block oligopolymeric structures of the aforementioned molecule families are likewise admirably suitable, but in such cases the amide-binding portion must be increased.

In the case of the preparation of shaped bodies in the form of tablets or sticks, the invention provides that the continuous phase is a macrogol(homopolyether), for example, PEG 1000, PEG 1500, PEG 2000, or PEG 4000, which in one embodiment is associated with low-molecular macrogols, for example, PEG 400 or PEG 200. This makes it possible to achieve very homogeneous distribution of the pharmaceutically active substance during dispersion, and it has been found to be particularly practical to dissolve the pharmaceutically active substance in low-molecular macrogols before adding it to the dispersion.

In an advantageous development of the invention, the continuous phase is composed of copolymers of said polymer types or emulsifier/polymer mixtures. This is particularly useful when, on the one hand, an active species is required to be introduced into the shaped body in a finely dispersed form in the interior of micelles only and, on the other hand, a slow release thereof to the environment is required. Furthermore, numerous other possible variations are feasible, particularly regarding the residence times of the shaped body in the cavity and also with reference to the release of the active substances or combinations of active substances to the environment.

Another feature of the invention also serves this end, in which the proportion of lipophilic component is between 25 and 50 wt % and preferably between 40 and 50 wt %, and the proportion of the continuous phase is from 40 to 70 wt % and preferably between 48 and 52 wt %. Thus the proportion of lipophilic phase, which usually contains the pharmaceutically active substances, is relatively large compared with the continuous phase. Wound healing is optimally assisted by the retarded release of active substance. Nevertheless the shaped body possesses adequate dimensional stability, for which reason it does not break when introduced into the cavity.

In one embodiment the lipophilic component used is a wax, particularly an ester of a long-chain fatty acid with a long-chain fatty alcohol, for example, officinal beeswax EuAB 98 or bleached beeswax EuAB 98, or the lipophilic component used is a fatty alcohol or a mixture of fatty alcohols, for example, stearyl alcohol or cetyl/stearyl alcohol.

The lipophilic component can be a triglyceride mixture, for example, a high-melting suppository composition having a melting point above 40° C. Alternatively, the lipophilic component used is a long-chain hydrocarbon mixture, for example, a higher-melting paraffin composition having a melting point above 40° C. Also suitable are ozocerites (hard paraffins) or mixtures of pharmaceutically useful fatty alcohols (cetyl/stearyl alcohols) as the retarding dispers matrix, which serve for delayed release of the active substances added to the shaped body at the site of action. In order to fix very non-polar active substances, use is made of mixtures of long-chain hydrocarbons, to great advantage.

The invention also includes selecting from a group of possible active substances and/or combinations of active substances, for example, pharmaceutical materials having anti-infective, antimicrobial, fungistatic or fungicidal, virustatic or virucidal action alone or together with steroidal antiphlogistics, local anesthetic agents, or anesthetic agents The concentration of active substances or combination of active substances should not exceed 10 wt %. The active substance present can be an antibiotic agent, e.g., benzyl penicillin procaine or gentamicin, an antiseptic agent, an antimycotic agent, and/or a virustatic agent, e.g., Aciclovir®. Alternatively, use can be made of a glucocorticoid, e.g., a hydrocortisol, its esters, a betamethason, its esters or a triamcinolone acctonide. A particularly good curative action is achieved when PVP iodine is incorporated as an active substance. Depending on the field of application, use may also be made of metronidazol. In addition, higher doses are conceivable in individual cases.

The geometry of the shaped bodies of the invention can be characterized in that the stick has a cylindrical conical or barrel-like shape. For example, the shaped body can have a cylindrical corpus of from 2 to 10 mm in diameter and from 40 to 100 mm in length in order to be suitable for administration in wound cavities and body cavities in humans and animals. Furthermore the shaped body can have the shape of a suppository or torpedo or be in the form of a tablet. Another possibility is the production thereof in suppository form (suppository or torpedo form or the like) or vaginal globulin form (vaginal tablets). Other shapes are realizable, depending alone on their end use.

The patent also relates to a process for the production of the shaped bodies of the invention. This is characterized in that at least one hydrophilic continuous phase, for example, a water-soluble or water-dispersible polymer (e.g., polyethers or polyesters of various molecular weights and compositions or emulsifiers of various molecular weights), is melted with at least one lipophilic component (e.g., waxes, triglycerides, or the like) acting as disperse phase, to form a melt, to which at least one active substance or a combination of active substances is added and the whole is mechanically dispersed under constant temperature conditions to form a composition. This is poured into a receptacle, vessel or the like, where it is cooled and stored for a specific period of time at constant temperature. The composition thus obtained is then heated to just below its softening point, plasticized by pressure or shearing, and compressed to a predefined shaped body, during which operation the operating pressure is not less than 50 bar, i.e. is for example at least 100 bar and the operating temperature is below the softening point of the composition.

According to the invention, there is added to a molten, low-molecular polymer the active substance or active substances or a combination of active substances, to which end this premix is dispersed and added to the melt, this having a favorable effect on the overall procedure.

It is important that the composition is cooled at a constant temperature gradient of at least 5° C./h. This prevents flocculation or crystallization of the individual components, which would make the shaped body brittle.

Expediently, the composition is compressed at a constant temperature and under a specific operating pressure to form dispersed solid shaped bodies, for which purpose preferably an extruder is used, by means of which the composition is compressed to produce extrudates of from 2 to 10 mm in diameter, which are then cut into lengths of from 40 to 100 mm.

The cylindrical shaped bodies produced by the process of the invention (sticks, styli medicinalis) have, compared with those produced by simple melting and subsequent pouring into casting molds, exceptionally high elasticity and fracture strength.

A significant development of the invention for which independent protection is claimed. According to said claim, a process for the production of compressed shaped bodies having a high content of low-melting hydrophobic components, or a process for the production of flowable or pourable pelletizable mixtures exhibiting a high content of low-melting hydrophobic components, is characterized in that small beads of a cooled melt are compressed, small spherules are pulverized and compressed, or a cooled powder is filled into capsules.

A pharmaceutical preparation is characterized by a solid dispersed fat in a polymer dispersion or a fat in a detergent dispersion.

Yet another object of the present invention is, finally, the use of dispersed solid shaped bodies containing active substances as pharmaceuticals in the teats of agricultural working animals, for example, milk-producing cows.

Other features, details, and advantages of the invention may be gathered from the wording of the claims and from the following description of working examples.

A shaped body of the invention possesses an amphiphilic continuous phase, for example, a biologically neutral oligomer of a polyether, a lipophilic component as the dispers phase, for example, an officinal beeswax EuAB 98 or bleached beeswax EuAB 98, and a water-soluble or fat-soluble active substance such as PVP iodine. The continuous phase and the lipophilic dispers phase dispersed therein form a dispersed "fat-in-polymer system", which can release the medically active substances dissolved therein to the environment at a retarded rate.

The shaped bodies are preferably sticks having diameters of from 2 to 19 mm, preferably from 2 to 10 mm, and lengths of from 40 to 100 mm, these sticks being characterized by high elasticity and bending strength by reason of their novel composition. They are used as pharmaceuticals for the treatment of diseases and injuries. In particular, they can be readily introduced into wound cavities, where the dissolved active substances are released.

The rate at which the active substance is released depends on the amount of lipophilic phase in the shaped body. It decreases as the amount of usable lipophilic phase increases. Heteropolymers and block heteropolymers (eg, copolymers) in a concentration of up to 70 wt % (advantageously from 48 to 52 wt %) as the continuous phase allow the introduction of lipophilic disperse phase in concentrations of up to 50 wt %. Under specific conditions, still higher percentages of the lipophilic phase are suitable to be used. Important representatives of these heteropolymeric alkoxamers are the polyethers poloxamer 124, poloxamer 188, poloxamer 237, poloxamer 338, and poloxamer 407. It is generally also possible to use ether-like polymers having a molecular weight of from 300 g/mol to 30,000 g/mol for the formulation.

Moreover, the release rate of the active substance is governed by the dwell time of the shaped body and the decomposition thereof in the destinated compartment, i.e. by the polymer selected for the continuous phase and its mechanical and chemical stability. Polymers which are labile in a physiological environment are degraded either by surface erosion or by hydrolytic cleavage over a period of time dependent on the polymer composition to form monomers which can be metabolized by the organism. The use of hydrolytically cleavable polymers allows for the control of the release rate of the pharmaceutically active substance to be governed not only by the dwell time of the shaped body in the organism or by the concentration of the disperse phase, but also by the stability of the shaped body. Degradable biologically acceptable polyesters, polyanhydrides, or polycarbonates in multifarious forms, as, for example, the combination of D-lactides and L-lactides, offer manifold possibilities of controlling the release kinetics of active species. Furthermore the biodegradable polyesters poly(dioxanone-co-$\epsilon$-caprolactone), poly(lactide-co-glycolide), poly(glycolide-co-trimethylene carbonate), poly(hydroxybutyrate-co-hydroxyvalerate), poly(trimethylene carbonate-co-$\epsilon$-caprolactone), poly(D/L-lactide-co-$\alpha$-caprolactone), and poly(glycolide-co-$\epsilon$-caprolactone), or the terpolymer poly(glycolide-co-trimethylene carbonate-co-p-dioxanone) are, for example, very suitable for this field of activity.

If a very slow release of the pharmaceutical is desired and/or if it is desired that only very slow or no degradation of the shaped body takes place in the organism due to fusion or decomposition, the concentration of the disperse phase must be very high and the polymer used should be relatively resistant to hydrolysis. In addition to polyethers, use is preferably made of polyamides and polymeric structures in which D-amino acid regions linked by peptide bonds are present.

If it is desired to make a shaped body from aggregating active substances or poorly solubilizable and emulsifiable pharmaceutical substances, in finely divided form, it is convenient to use, as the continuous phase, neutrally charged or non-ionic, biologically harmless detergents. It is advantageous to select representatives having a CMC greater than 6, as otherwise excessive foaming in the tissue compartment and lysis of cells may occur. For example, N-octylglucoside, dodecyl maltoside, or CHAPS may be used.

Especially when producing tablets and sticks, it is particularly advantageous to use polyethylene glycols. If PEG 1000, PEG 1500, PEG 2000, and PEG 4000 and furthermore PEG 200 or PEG 400 are used to form the continuous phase, the resulting dispersions can, after maturing, be processed, not only directly to compression moldings but also to small spherules or a powder. The powder can be placed in capsules or compressed to tablets. The beads can also be used to form a tablet having, however, a different type of fine distribution. PEG 200 and PEG 400, moreover, have the advantage that they can be used as low-molecular polyethylene glycols for wetting or dissolving the active species. This is carried out, where necessary, prior to the actual dispersing process.

The medical action of the shaped body of the invention may be described as follows:

Topical administration (for example, for wound disinfection, care of bite wounds, administration in the teats of milk-providing working animals and the like) of anti-infective agents, chemotherapeutants, antimicrobial, fungicidal, or virucidal pharmaceutically active substances by way of the shaped body, achieves a bacteriostatic or bacteriocidal, virucidal or fungicidal action at or in the desired compartment, i.e. the body cavity or wound cavity, which action is characterized by a high, uniform local concentration of active substance over a defined period of time (retarded liberation of active substance) and at the same time low systemic absorption of active substances.

The addition of steroidal antiphlogistic active substances (antiphlogistics) has a decongesting and anti-adhesive action. The addition of suitable analgesics or local anesthetics relieves wound pain.

The shaped body retarded, inter alia, by the lipophilic disperse phase remains at the site of action for hours and thus keeps the lumen of the compartment concerned open, which is of considerable advantage particularly when administering to teats. Adhesion of the tissue concerned is reliably avoided. There is a reduction of the secondary swelling occurring with an injury. The water-soluble or water-dispersible polymers used in the shaped body (predominantly polyethers and polyesters, alternatively emulsifiers and polyamides) are also secretion-absorbing and thus unfold an adjuvant antimicrobial action. In addition, they assist proliferation and thus accelerate wound healing.

Possible compositions of the shaped body are as follows:

| Example 1: | PVP iodine | 5.0 g |
| --- | --- | --- |
| | HC | 1.0 g |
| | poloxamer 188 | 79.0 g |
| | BW | 5.0 g |
| | ethyl alcohol 96% | 10.0 g |
| Example 2: | PVP iodine | 5.0 g |
| | HC | 1.0 g |
| | poloxamer 407 | 79.0 g |
| | BW | 5.0 g |
| | propylene glycol | 10.0 g |
| Example 3: | PVP iodine | 5.0 g |
| | HC | 1.0 g |
| | macrogol 1500 | 89.0 g |
| | BW | 5.0 g |
| Example 4: | PVP iodine | 5.0 g |
| | HC | 1.0 g |
| | poloxamer 188 | 46.0 g |
| | Witepsol 40 | 40.0 g |
| | ethyl alcohol 96% | 10.0 g |
| Example 5: | PVP iodine | 5.0 g |
| | HC | 1.0 g |
| | poloxamer 188 | 79.0 g |
| | BW | 5.0 g |
| | macrogol 400 | 10.0 g |
| Example 6: | PVP iodine | 5.0 g |
| | HC | 1.0 g |
| | poloxamer 188 | 77.5 g |
| | BW | 7.5 g |
| | macrogol 400 | 10.0 g |
| Example 7: | PVP iodine | 5.0 g |
| | HC | 1.0 g |
| | poloxamer 407 | 79.0 g |
| | BW | 5.0 g |
| | macrogol 400 | 10.0 g |
| Example 8: | PVP iodine | 5.0 g |
| | HC | 1.0 g |
| | poloxamer 407 | 77.5 g |
| | BW | 7.5 g |
| | macrogol 400 | 10.0 g |
| Example 9: | PVP iodine | 5.0 g |
| | HC | 1.0 g |
| | poloxamer 407 | 46.0 g |
| | Witepsol 40 | 40.0 g |
| | ethyl alcohol 96% | 10.0 g |

(BW = beeswax; HC = cortisol):

The individual steps of the manufacturing process of the invention can be described as follows:

1. The selected water-soluble or water-dispersible polymers or surfactants are melted together with the lipophilic component (eg, official beeswaxes, fatty alcohols, triglycerides), the processing temperature being governed by the melting points of the components used.

2. The pharmaceutically active substance(s) can be optionally dissolved or dispersed in a low-molecular macrogol (eg, PEG 200/400) or in alcohols conventionally used for pharmaceutical purposes, and then added to the melt or directly dispersed in the melt.

The pharmaceutically active substances used can be any of the pharmaceutically active substances which are suitable for administration in body cavities or wound cavities. Preference is given to the following groups of active agents: antibiotics, antiseptics, antimycotics, virustatics (anti-infective agents, chemotherapeutants), antiphlogistics, particularly glucocorticoids and anesthetic agents or local anesthetics, which can be added individually or in combination with each other in amounts or concentrations known to the person skilled in the art.

Particularly preferred antibiotics are penicillins, particularly benzyl penicillin procaine and gentamycin and their chemical derivatives, the preferred antiseptic agent being PVP iodine. The preferred glucocorticoids employed are hydrocortisol and its esters, betamethason and its esters, dexamethason and its esters, and triamcinolone (triamcinolone acctonide) and its esters. The preferred anti-infectious and antiprotozoal agent used is metronidazol, and the preferred virustatic agent used is Aciclovir®.

3. The mixtures of 1. and 2. are, if necessary, combined and mechanically dispersed, during which process the temperature should not fall below the melting temperature of the polymers used.

4. The dispersion melt is poured into a temperature-controlled vessel (e.g., a cylinder) and cooled to 15° C. under time control and then left to mature or cure for at least 4 hours at 15° C.

5. Following this period of cool storage, the dispersed solid composition thus obtained and containing active substance, is hydraulically extruded (extended) by means of a temperature-controlled high-pressure extruder at operating temperatures which must be from ca 5° to 10° C. below the softening point of the mixture used, to form shaped bodies via various nozzles or attached molds, the operating pressure being 100 bar.

In one embodiment, the manufacturing process is modified for the production of tablets and capsules. To this end, the pressure-loaded dispersion is converted by compression molding at a temperature below its softening point through a breaker plate to form small spherules. These are sifted and then compressed to tablets or ground to a powder with cooling. The latter is compressed to tablets or filled into capsules By combining physiologically acceptable polymers or emulsifiers with various conventional pharmaceutically acceptable fats, waxes, and fatty alcohols in a dispersed solid system, the drawbacks of the prior art, particularly the limits imposed by use of only polymers or fats or waxes may be overcome. Hitherto possible maximum concentrations of the lipophilic component are pushed up to higher values by the use of copolymers and block copolymers or their oligomeric variants, and this considerably influences the release rate of the active species. The solid fat-in-polymer dispersions or polymer-in-fat dispersions of the invention exhibit the material characteristics necessary for handling and administration and are at the same time a retarded pharmaceutical dosage form for administration in wound cavities and body cavities. The sticks show good physiological compatibly and degradability.

The process steps of the invention and their order of execution guarantee high and stable dispersity of the medical sticks, i.e. the degree of interdispersion of the materials and the interfacial affinity of the materials used toward each other is exceptionally high compared with conventional shaped bodies. The medical sticks form a homogeneous solid dispersion exhibiting all of the required properties.

The invention is not restricted to any of the embodiments described above but can be modified in diverse ways. For example, instead of a fat-in-polymer system, use may be made of a reverse system, ie a polymer-in-fat system. Furthermore non-lamellar phases and inverted systems comprising lipids, surfactants, or phospholipids can be used.

It is seen that water-soluble or water-dispersible polymers, particularly those of the family of compounds comprising the polyethers, polyesters, polyamides and/or detergents, and also lipophilic materials can readily form a dispersion by melting the components at suitable temperatures and admixing pharmaceutically active substances by mechanical procedures, i.e. a lipophilic dispers phase is distributed in a hydrophilic polymer phase as the continuous phase, to form a stable dispersion. By controlled cooling, curing, and storage followed by high-pressure molding or worm extrusion at defined temperatures and operating pressures, it is possible to produce, in addition to other types of shaped bodies, dispersed polymeric fatty sticks distinguished by particularly good fracture strength and flexibility. When used for medicinal purposes, such sticks have the advantage that the polymers and hydrophobic materials used for production (waxes, fatty alcohols, triglycerides etc.) are physiologically and toxicologically acceptable and any desired pharmaceutically active substances are suitable to be incorporated.

The combination of water-dispersible polymers with hydrophobic substances has the great advantage of delayed degradation of the dimensionally stable sticks in the desired physiological compartment, due to the lipophilic dispers matrix, which can only be slowly dissolved by endogenic liquids and secretions. This is accompanied by delayed but uniform release of active substance in the desired compartment, which ensures that there is an adequate therapeutic active level of pharmaceutically active substances over prolonged periods of time. Furthermore the slowly degrading stick corpus (shaped body) can maintain an injured body lumen, which is thus protected from undesirable adhesion.

All of the features and advantages, including structural details, spatial arrangements, and process steps, disclosed in the claims and description can be essential to the invention both independently and in a great variety of combinations.

The invention claimed is:

1. A method of treating wounds in milk producing organs of agricultural animals comprising the steps of:
   providing a fracture-stable shaped body possessing flexural elasticity, having a length of up to 100 mm and a diameter of 2 mm or more, and including PVP iodine together with a poloxamer, and comprising at least one amphiphilic continuous phase and at least one lipophilic component as a disperse phase, and also comprising at least one pharmaceutically effective water-soluble or fat-soluble material as an active substance, wherein the continuous phase is a poloxamer and the portion of continuous phase is at least 40 wt % and the proportion of the disperse phase is up to 50 wt %, and
   introducing the shaped body into at least one milk-producing organ of an agricultural working animal for wound treatment.

* * * * *